(12) United States Patent
Avar et al.

(10) Patent No.: US 6,201,047 B1
(45) Date of Patent: Mar. 13, 2001

(54) METHOD OF STABILIZING EPDM MODIFIED POLYPROPYLENE BY ADDING PIPERIDINE COMPOUNDS

(75) Inventors: Lajos Avar, Biel-Benken (CH); Andreas Thuermer, Huningue; Gilbert Ligner, Wintzenheim, both of (FR)

(73) Assignee: Clariant Fianance (BVI) Limited, Muttenz (CH)

( * ) Notice: Subject to any disclaimer, the term of this patent is extended or adjusted under 35 U.S.C. 154(b) by 0 days.

(21) Appl. No.: 09/011,932

(22) PCT Filed: Aug. 16, 1996

(86) PCT No.: PCT/EP96/03622

§ 371 Date: Feb. 17, 1998

§ 102(e) Date: Feb. 17, 1998

(87) PCT Pub. No.: WO97/07159

PCT Pub. Date: Feb. 27, 1997

(30) Foreign Application Priority Data

Aug. 18, 1995 (DE) ............................................. 195 30 468

(51) Int. Cl.[7] ..................... C08K 5/3435; C08F 126/06; C07D 211/34
(52) U.S. Cl. .......................... 524/102; 526/263; 526/265; 546/187
(58) Field of Search .................................. 546/427, 428, 546/187; 524/102; 526/263, 265

(56) References Cited

U.S. PATENT DOCUMENTS 5,021,478 * 6/1991 Ravichandran et al. ................ 525/91
5,705,545 * 1/1998 Avar et al. ............................ 524/102

FOREIGN PATENT DOCUMENTS

3412227 * 11/1984 (DE) .

* cited by examiner

Primary Examiner—Alan L. Rotman
Assistant Examiner—Rita Desai
(74) Attorney, Agent, or Firm—Hesna J. Pfeiffer; Scott E. Hanf

(57) ABSTRACT

The invention relates to the use of piperidine compounds of the formula I

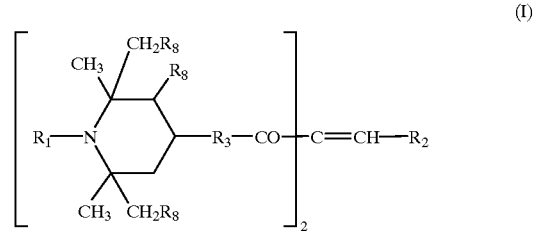

in which $R_1$ is hydroxyl, lower alkyl, lower alkoxy, $R_2$ is a substituted or unsubstituted, mono- or bicyclic radical of aromatic type, $R_3$ is oxygen, —NH— or —N($C_{1-4}$-alkyl)- and $R_8$ independently at each occurrence is hydrogen or methyl for preparing light-stabilized, EPDM-modified polypropylene which is employed in particular in automotive construction, such as for shock absorbers, cover strips and the like. A further subject of the invention is the combination of abovementioned piperidine compounds with known UV absorbers. The invention also relates to EPDM-modified polypropylene which contains from 0.05 to 2.5% by weight, preferably from 0.1 to 0.6% by weight, of a radical of a compound of the above formula I, and to products produced therefrom.

10 Claims, No Drawings

METHOD OF STABILIZING EPDM MODIFIED POLYPROPYLENE BY ADDING PIPERIDINE COMPOUNDS

This is a 371 of PCT/EP96/03622 filed on Aug. 16, 1996.

The invention relates to the subject-matter of the Patent claims.

The light stabilization of mouldings of EPDM-modified polypropylene in automotive construction, especially of car bumpers, is a particularly demanding task owing to the heterogeneous composition of the polymer matrix and its partial crystallinity, since (a) the migration of the light stabilizer to the surface must be prevented and (b) the light stabilization must be secured at a high level with good permanence over a long period of time.

The object of the present invention, therefore, was to stabilize EPDM-modified polypropylene, which is used in particular in automotive construction, against the effect of light.

This object is achieved, and the prior art greatly exceeded, by the present invention. It has in fact been found that the migration of the stabilizer can be prevented if it is bound chemically to the EPDM-modified polypropylene. Chemical binding to the EPDM-modified polypropylene takes place by exposing the EPDM-modified polypropylene comprising the novel stabilizer of formula I below to high-energy light, the bond to the surface of the polymer and/or within the polymer matrix being formed in layers close to the surface. Light stabilization at a high level is ensured in that the stabilizer compounds, which are located in the interior of a moulding produced from EPDM-modified polypropylene comprising novel stabilizer compounds, diffuse slowly to the surface where they are bound chemically to the EPDM-modified polypropylene by the exposure which occurs in the course of service. Thus any destroyed stabilizer compounds are immediately replaced at the surface and the high permanence of the UV stabilization is maintained.

The invention therefore provides for the use of piperidine compounds of the formula I

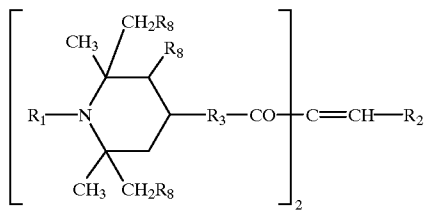

(I)

in which $R_1$ is hydrogen, hydroxyl, lower alkyl, lower alkoxy, acyl or oxygen $R_2$ is a substituted or unsubstituted, mono- or bicyclic radical of aromatic type, $R_3$ is oxygen, —NH— or —N($C_{1-4}$-alkyl)- and $R_8$ independently at each occurrence is hydrogen or methyl for producing light-stabilized, EPDM-modified polypropylene which is employed in particular in automotive construction, such as for shock absorbers, cover strips and the like.

By lower alkyl are meant preferably radicals having 1–8, especially 1 or 2, carbon atoms; suitable acyl radicals are preferably those of formic, acetic or propionic acid.

All radicals $R_1$ are preferably hydrogen, hydroxyl, methyl or $C_{1-8}$-alkoxy, especially hydrogen or methyl, in particular methyl.

Examples of suitable mono- or bicyclic radicals $R_2$ of aromatic type are benzene, naphthalene and nitrogen- and/or sulphur-containing five- or six-membered rings with or without a fused-on benzene ring which carry, for example, sterically hindered hydroxyl as substituents (3,5-di-tert-butyl-4-hydroxyphenyl), or a thienyl radical. Aromatic six-membered rings are preferred. Examples of possible substituents on these rings are hydroxyl, lower alkyl or alkoxy, preferably methyl, tert-butyl, methoxy, ethoxy, hydroxyl and one or two further groups of the formula

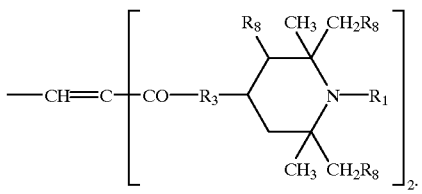

Every $R_8$ is preferably hydrogen.

Additional stabilizers which can be employed for the EPDM-modified polypropylene include antioxidants, for example sterically hindered phenols, secondary aromatic amines or thioethers (described, for example, in "Plastics Additives", Gachter and Muller, 1985, pp. 8–12), further HALS compounds, antistatic agents, flame retardants, plasticizers, nucleating agents, metal passivators, biocides and the like.

The invention also provides for the combination of piperidine compounds of the formula I with known UV absorbers (2-(2'-hydroxyphenyl)benzotriazole compounds, 2-hydroxybenzotriazole compounds, 1,3-bis(2'-hydroxybenzoyl)benzenesalicylates, cinnamic acid derivatives, triazine derivatives and oxalanilides). It has been found that by mixtures of compounds of the formula I and UV absorbers in a ratio of from 10:1 to 1:10, preferably from 4:1 to 1:4, depending on the thickness of the article to be stabilized, the equilibrium between diffusion rate and photochemical binding of stabilizers of the formula I to the polymer matrix can be influenced and thus the light stabilization effect improved.

The following compounds of the formulae Ia and Ib are particularly suitable for the light stabilization of EPDM-modified polypropylene:

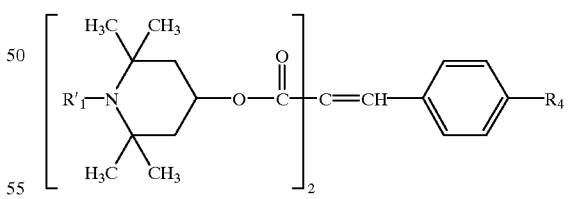

(Ia)

in which $R_4$=H, $OCH_3$ $R'_1$=H, $CH_3$, $OC_8H_{17}(n)$,

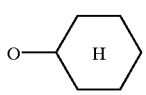

and

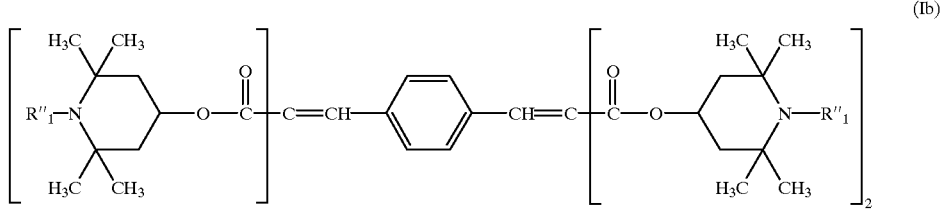

in which
R"$_1$=H, CH$_3$.

Chemical binding to the EPDM-modified polypropylene takes place during service and thus in the course of exposure of the EPDM-modified polypropylene comprising the novel piperidine compound to high-energy visible or near UV light, the period of exposure necessary for this generally being between about 100 and 400 hours. Exposure can take place with a xenon lamp or with sunlight. Under such exposure, the double bonds in the compound of the formula I are broken and chemical bonding takes place to appropriately reactive carbon atoms of the EPDM-modified polypropylene.

In the case of bulky mouldings such as car bummers, the HALS compounds in the interior of the mouldings (that is, the piperidine compounds or piperidine radicals which act as stabilizer) will diffuse slowly towards the surfaces where they are bound chemically to the EPDM-modified polypropylene as a result of the exposure which occurs in the course of service. In this way, any destroyed HALS stabilizers at the surface are continually replaced and stabilization is extended for a substantially longer time.

In general use is made of from 0.05 to 2.5%, preferably from 0.1 to 0.6k, of one or more compounds of the formula I, based on the weight of the EPDM-modified polypropylene to be stabilized and depending on the target level of stabilization or on the service life (1, 2 or 10 years) or geographical area of deployment of the finished polymer article.

Polymer articles which have been stabilized in accordance with the present invention against the damaging effect of UV light have the feature, not found in the prior art, that after only a short period of service and thus of exposure to light it is no longer possible to remove the stabilizers (compounds of the formula I) from the EPDM-modified polypropylene by physical means, even by eluting with solvents. With the conventional use of the polymer articles the leaching, i.e. the loss of stabilizers, can be attributed to climatic and/or environmental influences (for example, contact with cleaning liquids, oils, fats or other chemicals). Even under these conditions the polymers UV-stabilized in accordance with the invention exhibit a high resistance. In general, EPDM-modified polypropylene with a basic level of stabilization is employed as the base material and is UV-stabilized in accordance with the invention in a second processing step. Basic stabilization is generally carried out, as is known, with 0.05–0.2% of a phenolic antioxidant and 0.05–0.5% of calcium stearate, based on the weight of the EPDM-modified polypropylene.

The preparation of compounds of the formula I [likewise those of the formula (Ia) and (Ib)] is known and takes place by condensation of one mole of the compound of the formula II $$R_2—CH=C=(COOH)_2 \quad (II)$$

or of a functional acid derivative, for example a low molecular mass ester or an acid halide, with 2 mol of a compound of the formula III

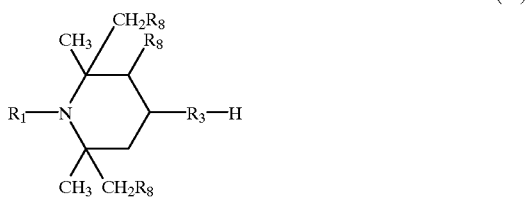

In the examples below the parts and percentages are by weight. The parts by volume correspond to the volume of equal parts by weight of water. The temperatures are indicated in degrees Celsius.

I. Preparing compounds of the formula I

EXAMPLE 1

84 parts of dimethyl para-methoxybenzalmalonate are dispersed with 154 parts of 1,2,2,6,6-pentamethyl-4-hydroxypiperidine in 80 parts of xylene, the dispersion is heated to 800, 0.5 part by volume of tetraisopropyl orthotitanate is added, and the mixture is stirred at about 140° for 22 hours while distilling off the methanol which is formed. The reaction solution is then cooled to 80°, washed three times with 150 parts of water, the organic phase is separated off, the solvent is removed by distillation and the residue is recrystallized from ethanol. The resulting product of the formula I

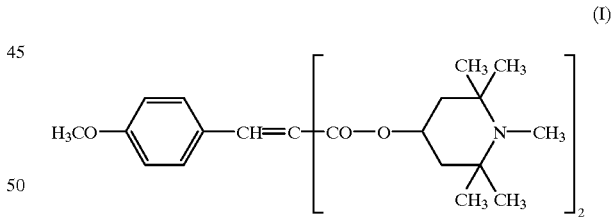

melts at 120–125°.

II. Preparing EPDM-modified polypropylene with basic stabilization

EXAMPLE 2

An EPDM-modified polypropylene consisting of 55–70% ethylene, 28–43% propylene and 1.8–3.3% hexadiene, dicyclopentadiene or ethylvinylidene (crosslinked by sulphur vulcanization or free-radically by addition of peroxide), which has a melt index of 10 dg/min (2300/2.16 kg), and the three basic stabilizers below were used to prepare a free-flowing dry mix which was subsequently processed in a single-screw extruder (l:d=20, compression ratio 1:3, screw diameter=20 mm, 50 revolutions per minute) at 230°.

Basic stabilization:

| | |
|---|---|
| 800 ppm of Irganox ® 1010 | (Ciba-Geigy), an antioxidant based on a sterically hindered phenol |
| 1000 ppm of Sandostab ®P-EPQ | (Clariant), a processing stabilizer based on a sterically hindered phosphonite |
| 800 ppm of calcium stearate. | |

EXAMPLE 3

An EPDM-modified polypropylene (crosslinked by sulphur vulcanization or free-radically by addition of peroxide) with an EPDM rubber content of 20–25%, which has a melt index of 6 dg/min (2300/2.16 kg), and the two basic stabilizers below were used to prepare a free-flowing dry mix which was compounded in a single-screw extruder (l:d=20, compression ratio 1:3, screw diameter=20 mm, 50 revolutions per minute) at 230°.
Basic stabilization:

| | |
|---|---|
| 1500 ppm of Irganox ® B-225 | (Ciba-Geigy), an antioxidant comprising equal parts of Irganox 1010 (see above) and Irgafos ® 168, a phosphite processing stabilizer |
| 800 ppm of calcium stearate. | |

EXAMPLE 4

An impact-modified polypropylene block copolymer with an ethylene content of 4% and a melt index of 5.0 dg/min (2300/2.16 kg) was stabilized with the following three basic stabilizers.
Basic stabilization:

| | |
|---|---|
| 1000 ppm of Irganox ® 1010 | (Ciba-Geigy), an antioxidant based on a sterically hindered phenol |
| 500 ppm of Sandostab ®P-EPQ | (Clariant), a processing stabilizer based on a sterically hindered phosphonite |
| 1000 ppm of calcium stearate. | |

III. EPDM-modified polypropylene stabilized in accordance with the invention
The following measurements were carried out on polypropylene stabilized i) in accordance with the invention and ii) in accordance with the prior art:
a) Artificial weathering in accordance with DIN 52231-A:
  Assessment is made visually with regard to surface deterioration or surface cracks, gloss, elasticity, flexibility and discoloration.
b) Long-term thermal ageing test in accordance with DIN 53383
  The fault criterion is the bending test of injection moulded sheets following storage in a convection oven, i.e. the fracture of the sample on assessment.
c) Accelerated weathering in accordance with DIN 53231-A
  The failure of the samples is assessed on the basis of mechanical measurements:
    thin samples: tensile strength in accordance with DIN 53455
    thick test sheets: impact strength in accordance with DIN 53453

The injection moulded sheets and test rods were produced with an injection moulding machine of the type Ahrburg IM at a temperature of 220–230°, 80 revolutions per minute, an injection pressure of 100 bar and a closing force of 12 kN.

EXAMPLE Aa AND COMPARATIVE EXAMPLE Ab

Injection moulded test sheets 2 mm thick, produced from the basically stabilized EPDM-modified polypropylene from Example 2, to which the following compounds have been added in addition as light stabilizers, were subjected to artificial weathering.

| Example | Light stabilizer | Failure after |
|---|---|---|
| Aa | 4500 ppm of compound 1 from Example 1 | 3500 h |
| Ab | 5000 ppm of Sanduvor ® 3944* | 2500 h |

*Sanduvor ® 3944 is a light stabilizer having a mean molecular weight of >2500 and a melting range of 100–135° from Clariant, of the formula

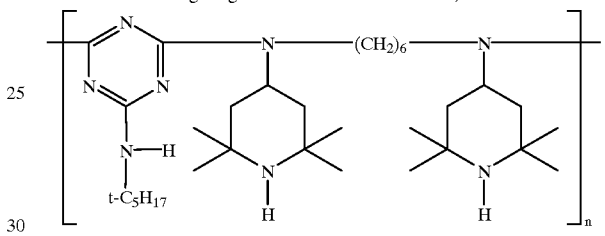

The present comparison indicates a markedly better service life of the sample Aa stabilized in accordance with the invention (despite a 10% lower concentration deployed) relative to material Ab, treated with customary commercial HALS compound, in accordance with the present state of the art.

EXAMPLE Ba AND COMPARATIVE EXAMPLES Bb–Bd

Long-term thermal ageing was measured on injection moulded test sheets 3 mm thick produced from basically stabilized EPDM-modified polypropylene from Example 3 to which the following light stabilizers were added:

| Example | Light stabilizer | Failure after |
|---|---|---|
| Ba | 4500 ppm of compound from Example 1 | 30 days |
| Bb | 5000 ppm of Sanduvor ® 3944 | 14 days |
| Bc | 3000 ppm Tinuvin ® 770* 2000 ppm Sanduvor ® 3944 | 14 days |
| Bd | 6000 ppm Tinuvin ® 770 | 7 days |

*Tinuvin ® 770 is a light stabilizer from Ciba-Geigy, of the formula

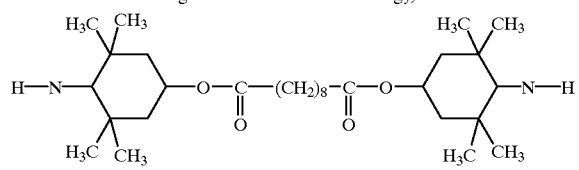

EXAMPLES Da TO Dc AND COMPARATIVE EXAMPLES Dd TO De

An accelerated weathering test was carried out on injection moulded test specimens (1 mm dumb bells or 3 mm test sheets) produced from the basically stabilized, high-impact polypropylene block copolymer from Example 4 to which the following light stabilizers were added:

| Ex. | Light stabilizer HALS | UV absorber UVA | Tensile strength (in % of original value) | Impact strength |
|---|---|---|---|---|
| Da | 2000 ppm of compound 1 | — | 73% after 3500 h | 88% |
| Db | 1330 ppm of compound 1 | 1330 ppm Sanduvor ® 3035* | 96% after 3500 h | 90% |
| Dc | 600 ppm of compound 1 | 2260 ppm of Sanduvor ® 3035 | 95% after 3500 h | 98% |
| Dd | 2000 ppm Sanduvor ® 3944 | — | 50% after 3000 h | 57% |
| De | — | 4000 ppm Sanduvor ® 3035 | 50% after 2900 h | 80% |

*Sanduvor ® 3035 is a UV absorber from Clariant, having the formula

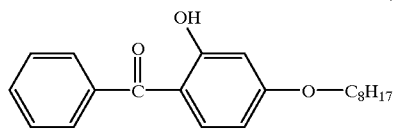

The concentration ranges chosen for Uv absorbers in the above example take account of the known fact that UV absorbers, owing to their markedly lower activity as light stabilizers in comparison with HALS compounds, must be employed in approximately twice the concentration in the polymer in order to obtain approximately comparable light stabilizing effects in relatively thick articles as described in the present example (see Example De as against Da and Dd). The examples Db (50% HALS, 50% UVA) and Dc (20% HALS, 80% UVA) emphasize the outstanding activity of combinations of novel light stabilizers of the HALS type with UV absorbers, which is clearly expressed in the very small changes in mechanical properties after exposure, i.e. in the efficient UV stabilization of the polymer.

What is claimed is:

1. A method of stabilizing, EPDM-modified polypropylene by adding piperidine compounds of the formula I

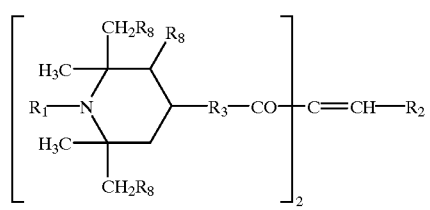

in which $R_1$ is lower alkyl, $R_2$ is a substituted or unsubstituted, mono- or bicyclic radical of aromatic type, $R_3$ is oxygen, —NH— of —N($C_1$-4-alkyl)- and $R_8$ independently at each occurrence is hydrogen or methyl to EPDM-modified polypropylene for producing light-stabilized, EPDM-modified polypropylene for automotive construction.

2. A method of stabilizing, EPDM-modified polypropylene according to claim 1 characterized in that said compound of the formula I is further defined as:

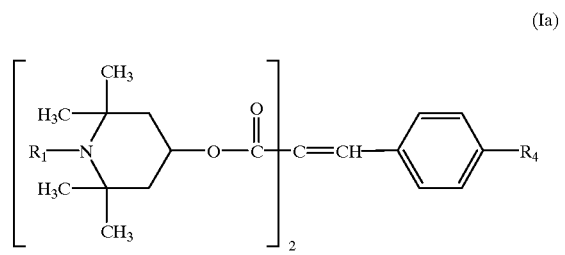

in which $R'_1$=$CH_3$, $R_4$=H, $OCH_3$.

3. A method of stabilizing, EPDM-modified polypropylene according to claim 1, characterized in that said compound of the formula I is further defined as:

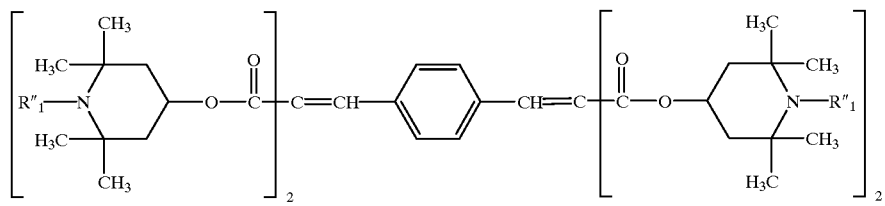

in which $R''_1$=H, CH3.

4. A method of stabilizing, EPDM-modified polypropylene according to claim 1, further comprising adding a UV absorber so that a mixture of compounds of the formula I and UV absorbers is in a ratio of from 10:1 to 1:10.

5. A method of stabilizing, EPDM-modified polypropylene as claimed in claim 1, wherein an amount of a radical of the compound of formula 1 added is from 0.05 to 2.5% by weight.

6. A method of stabilizing, EPDM-modified polypropylene, as claimed in claim 1, wherein an amount of a radical of the compound of formula 1 added is from 0.1 to 0.6% by weight.

7. A method of stabilizing, EPDM-modified polypropylene for automotive construction according to claim 4, wherein said ratio of compounds of the formula I and UV absorbers is from 1:4 to 4:1.

8. EPDM-modified polypropylene produced according to the method of claim 5.

9. EPDM-modified polypropylene produced according to the method of claim 6.

10. EPDM-modified polypropylene produced according to the method of claim 4.

* * * * *